United States Patent
Cann et al.

Patent Number: 5,676,643
Date of Patent: Oct. 14, 1997

[54] DISPENSER FOR FRIABLY RELEASING DRY PARTICULATE MEDICAMENTS

[75] Inventors: David V. Cann, Surrey, England; Robert S. Dirksing, Cincinnati, Ohio

[73] Assignee: The Procter & Gamble Company, Cincinnati, Ohio

[21] Appl. No.: 387,549

[22] Filed: Feb. 13, 1995

[51] Int. Cl.⁶ .................................................. A61M 35/00
[52] U.S. Cl. .............................. 604/1; 604/289; 604/290; 604/309
[58] Field of Search ............................. 604/289, 290, 604/292, 293, 303, 304, 309, 1, 2, 46, 57, 58; 132/293, 320, 317, 318; 401/98

[56] References Cited

U.S. PATENT DOCUMENTS

| | | | |
|---|---|---|---|
| 1,687,472 | 10/1928 | Dorman et al. | |
| 2,470,297 | 5/1949 | Fields | 128/266 |
| 2,590,832 | 3/1952 | Brown | 128/206 |
| 2,594,093 | 4/1952 | Thompson | 128/272 |
| 3,666,182 | 5/1972 | Cureton | 239/327 |
| 3,828,802 | 8/1974 | Spanel | 132/9 |
| 3,948,265 | 4/1976 | Al Ani | 128/267 |
| 3,980,074 | 9/1976 | Watt et al. | 128/2 A |
| 4,017,007 | 4/1977 | Riccio | 222/80 |
| 4,177,811 | 12/1979 | Alvarez | 128/261 |
| 4,423,724 | 1/1984 | Young | 128/203.15 |
| 4,457,756 | 7/1984 | Kern et al. | 604/286 |
| 4,557,720 | 12/1985 | Hemphill | 604/1 |
| 4,610,556 | 9/1986 | Tsai | 401/18 |
| 4,627,432 | 12/1986 | Newell et al. | 128/203.15 |
| 4,645,487 | 2/1987 | Shishov et al. | 604/58 |
| 4,747,842 | 5/1988 | Dietz | 604/309 |
| 4,811,731 | 3/1989 | Newell et al. | 128/203.15 |
| 4,838,851 | 6/1989 | Shabo | 604/1 |
| 4,860,740 | 8/1989 | Kirk et al. | 128/203.15 |
| 4,915,234 | 4/1990 | Boeller | 206/581 |
| 5,046,493 | 9/1991 | Kropkowski et al. | 128/203.15 |
| 5,069,232 | 12/1991 | Staar | 132/320 |
| 5,221,153 | 6/1993 | Spatz | 401/98 |

FOREIGN PATENT DOCUMENTS

| | | |
|---|---|---|
| 481 666 A1 | 10/1991 | European Pat. Off. |
| 558 879 A1 | 3/1992 | European Pat. Off. |
| 481666A1 | 4/1992 | European Pat. Off. |
| WO 93/22065 | 4/1993 | WIPO |

*Primary Examiner*—John G. Weiss
*Assistant Examiner*—Dennis Ruhl
*Attorney, Agent, or Firm*—Ronald W. Kock; Michael E. Hilton; Daniel F. Nesbitt

[57] ABSTRACT

A single-use disposable, applicator for dispensing it dry medicament in particulate form, having an applicator surface, a handle for manually supporting the applicator surface and a dry medicament friably bonded to the applicator surface such that a predetermined quantity of the substantially dry medicament is substantially immediately released upon exposure to a friction, or electrostatic discharge, or both.

7 Claims, 5 Drawing Sheets

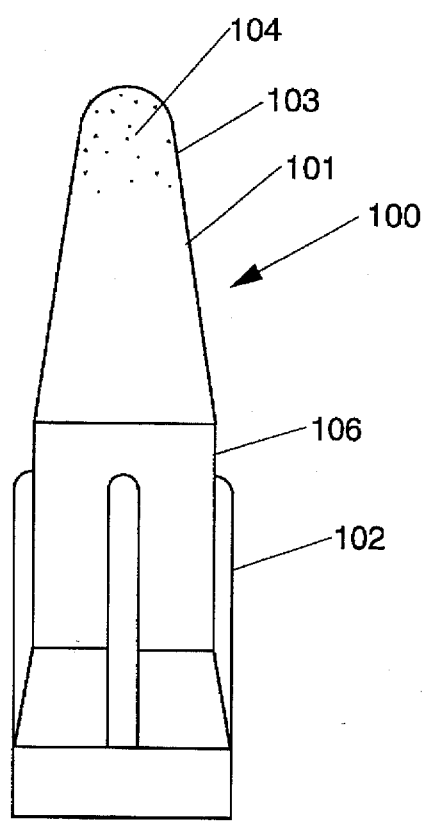
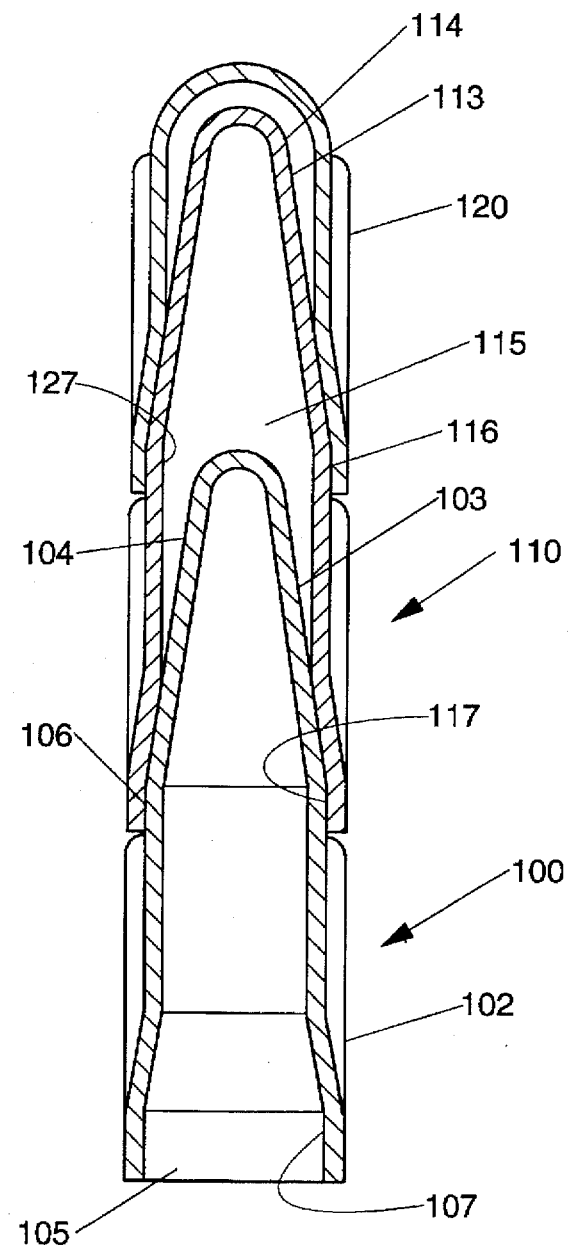
Fig. 10
Fig. 11

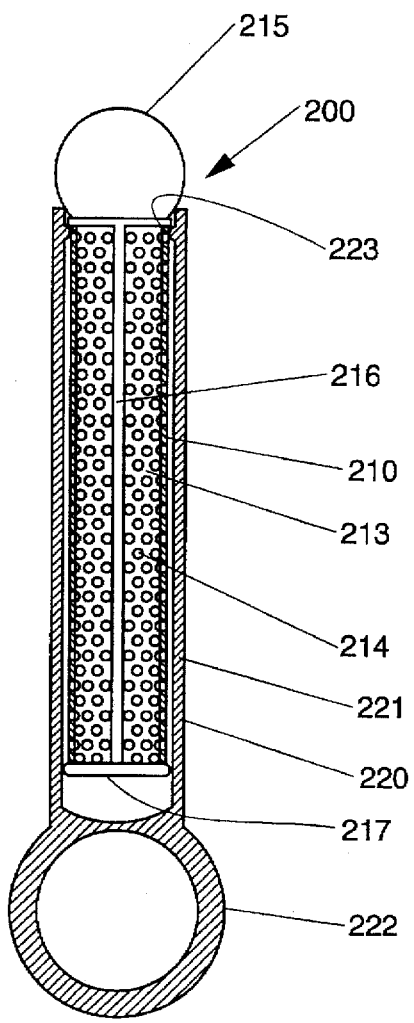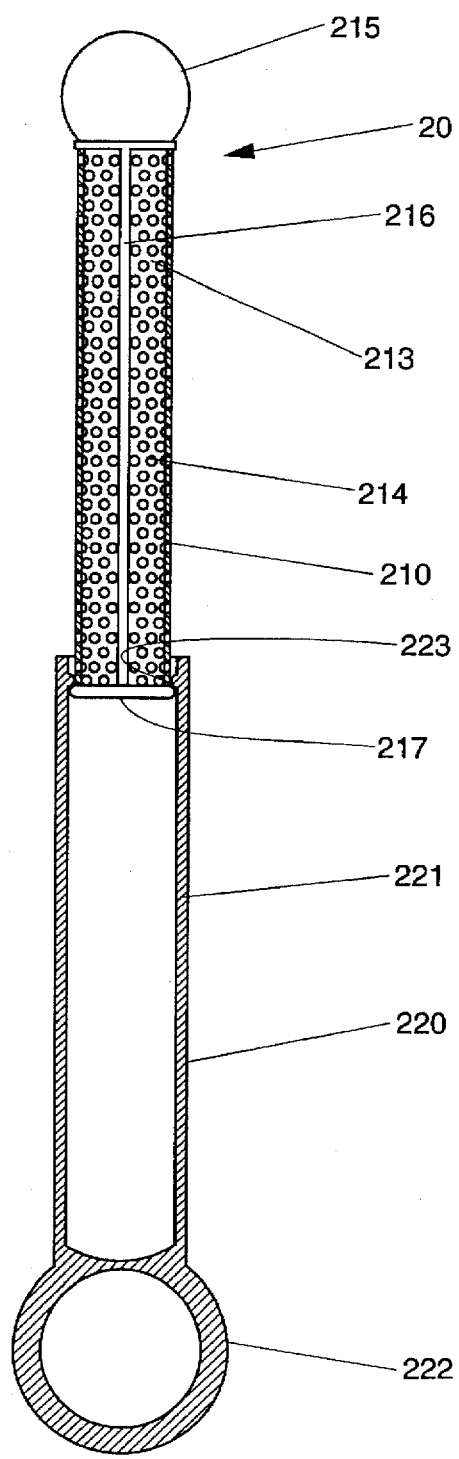
Fig. 12
Fig. 13

DISPENSER FOR FRIABLY RELEASING DRY PARTICULATE MEDICAMENTS

BACKGROUND OF THE INVENTION

1. Field of the Invention

The present invention relates to dispensers for delivering dry particulates; more particularly, to such dispensers utilizing an applicator surface to deliver and dispense a predetermined dose of particulates to a target surface; and even more particularly, to such dispensers for delivering a medicament to a body tissue.

2. Description of the Prior Art

There are many examples of dosing medicament delivery systems in the art and in the market place, most of them for liquid medicaments. Many of the liquid dose delivery systems use a simple pressurized container and dosing valve to provide multiple individual predetermined doses of liquid medicaments from a supply within the container. Examples include the metered spray devices often utilized for nasal decongestants and/or antihistamines. Additionally, single-use applicators have also been utilized to deliver liquid medicaments. For example, wetted swab-type applicators which utilize a solvent fluid are disclosed in U.S. Pat. No. 1,687,472 issued to Dorman on Oct. 9, 1928.

On the other hand, dry medicaments offer many advantages over liquid medicaments. For example, dry medicaments maintain their properties and activity much longer than in their solubilized liquid state. Further, providing medicaments in the dry state may eliminate the need for additional ingredients; e.g., carriers, solvents and/or preservatives. Additionally, such dry medicaments—especially without the carriers solvents and/or preservatives—are absorbed quicker by the target body tissues, since the medicament is not diluted by these additional ingredients. Also important, is the current mandate to eliminate fluorocarbon propellants which are often key to the simplicity of liquid delivery systems.

Delivering a dry medicament, however, has its own difficulties. One approach which has been used to deliver dry medicaments is to provide a multi-use dispensing device for dispensing a particulate (e.g., powdered) medicament. Because dry powdered medicaments don't flow like a liquid, they are more difficult to accurately meter. Moreover, once the particulate medicament is metered, it must somehow be transferred from the metering chamber to the intended body tissue. Consequently, previous attempts at providing accurate dosing of particulate, especially powdered, medicaments from multiple dose delivery systems have been complex, expensive, and/or clumsy for the user.

Another approach for delivering dry medicaments which eliminates the dosing problems associated with multiple use dispensers has been to provide a single-use, disposable, dosing device. Such dosing devices overcome the problem of providing accurate dosing, since the metering of the medicament is accomplished during manufacturing. Consequently, such dosing devices need only accomplish the actual transfer of the particulate medicament to the intended body tissue. One method to transfer the medicament involves coating a portion of an applicator with a very thin, homogenous layer of medicament in a dried but liquid soluble state and delivering the active via allowing the moisture from a moist body area to dissolve the medicament layer; transferring the medicament to the body tissue. An example of a device utilizing this method is U.S. Pat. No. 3,948,265 issued to Al Ani. on Apr. 6, 1976. A major disadvantage of such a method is the requirement of prolonged contact with a moist body area such that the medicament layer is dissolved. Furthermore, sufficient moisture must be present to effect dissolution of the medicament layer to provide transfer of the medicament.

SUMMARY OF THE INVENTION

In accordance with one aspect of the present invention, an applicator for dispensing a dry medicament in particulate form is provided. The applicator includes an applicator surface and a dry medicament. A bond friably attaches the dry particulate medicament to the applicator surface such that a predetermined quantity of the substantially dry medicament is substantially immediately released upon exposure to a friction, or electrostatic discharge, or both.

In accordance with another aspect of the present invention, a single-use disposable applicator for dispensing a predetermined quantity of a dry medicament is provided. The applicator comprehends an applicator body including a disposable applicator surface and a handle for manually supporting the applicator surface. The applicator also comprehends a dry medicament friably attached to the applicator surface such that a predetermined quantity of the substantially dry medicament is substantially immediately released in particulate form upon exposure to fiction, electrostatic discharge, or both.

In accordance with another aspect of the present invention, a method of delivering a dry medicament in particulate form from an applicator surface is provided. The method includes friably attaching a dry medicament to the applicator surface such that a predetermined quantity of the dry medicament is substantially immediately released in response to friction, or electrostatic discharge, or both. Then, substantially immediately releasing a predetermined quantity of the dry medicament by exposing the dry medicament friably attached to the applicator surface to fiction, or electrostatic discharge, or both.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings, in which like reference numerals identify identical elements and wherein;

FIG. 8b is a top plan view of the dispenser of FIG. 8a;

FIG. 10 is a side view of a fifth alternative preferred embodiment of a dispenser of the present invention; and FIG. 11 is a cross-sectional view of a set of dispensers of FIG. 10 shown in a nested and stacked condition.

FIG. 12 is a cross-sectional view of a sixth alternative preferred embodiment of a dispenser of the present invention having a protective telescoping sheath.

FIG. 13 is a cross-sectional view of the dispenser of FIG. 12, but having the protective telescoping sheath in the extended condition.

DESCRIPTION OF THE PREFERRED EMBODIMENT

Figure 1:
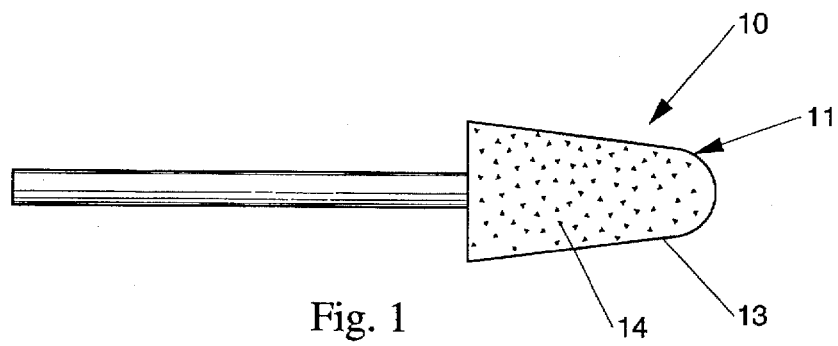
FIG. 1 is a side view of a preferred embodiment of a dispenser for friably releasing a dry particulate medicament of the present invention.

In a particularly preferred embodiment seen in FIG. 1, the present invention provides a dispenser, generally indicated as 10. As illustrated, dispenser 10 is a single-use, disposable unit dose dispenser which is particularly well suited for delivering particulate medicaments 14 to the nasal cavity. Although particular cavities are referred to herein, dispenser 10 may be adapted to deliver medicaments 14 to any body tissue, including the mucous membranes of the nasal, oral, vaginal, and anal passages. Dispenser 10 includes an applicator body 11 and a handle 12. Applicator body 11 further includes an applicator surface 13 which, in this embodiment, has a generally frustro-conical shape. Applicator surface 13 is preferably liquid-resistant such that any available moisture on the surrounding body tissue (e.g., on a mucous membrane) will not be absorbed by applicator surface 13 during the application process.

A dry medicament 14 is friably attached to applicator surface 13. As used herein, "friably" attached means that the attachment of medicament 14 to applicator surface 13 is strong enough to withstand the forces generally encountered during manufacturing and distributing of disposable dose dispenser 10; while simultaneously being sufficiently weak to substantially immediately release a predetermined unit dose of particulate medicament 14 from applicator surface 13 during application. The release from applicator surface 13 may be caused by friction (e.g., light mechanical action or inspired air) and/or electrostatic discharge. Preferably, the release is caused by the light mechanical action of actual physical contact; e.g., contact with a mucous membrane, or contact with hair in the nasal cavity analogous to the transfer of pollen from the anther of a flower to the legs or abdomen of bees in the pollination process.

In addition to the substantially immediate release aspect of the friably attached medicament 14, the friably attached nature of medicament 14 results in the medicament being released in particulate form; e.g., as powders, flakes, granules, and agglomerated particles (including the result of ink jet printing the medicament onto the surface). Although the size of the particulate elements depends upon the particular application, they are preferably less than about 1 millimeters; more preferably, less than about 100 microns.

Exemplary mechanisms to friably attach medicament 14 to applicator surface 13 to provide substantially immediate release of a predetermined unit dose quantity of particulate medicament include electrostatic attraction, dipole attraction, adhesive, ionic bonding, polar bonding, or the like. An example discussed hereinafter in more detail involves ink jet printing a solubilized medicament onto applicator surface 13 as agglomerated particles which are so lightly bonded they readily come off applicator surface 13. Other examples discussed in more detail hereinafter involve adhering particulate medicament 14 to applicator surface 13 with an adhesive. The adhesive may be relatively light such that the entire particulate readily comes off applicator surface 13. Alternatively, the adhesive may be relatively heavy, and the particulate relatively frangible such that a portion of each particulate can readily break off to release the unit dose of particulate medicament 14.

As another example, the illustrated dispenser 10 may utilize electrostatic attraction to friably attach a substantially dry particulate medicament 14 to applicator surface 13. An induced charge, or even the natural residual charge of molded polypropylene may be utilized to attract and friably attach particulate medicament 14 to applicator surface 13. One way to utilize an induced charge could include dissipating any initial residual electrostatic charge on applicator surface 13 by rotating applicator surface 13 against an earth ground. Subsequent to grounding, dispenser 10 can be rotated about its central axis with applicator surface 13 in contact with a silk cloth; the rubbing action thereby inducing an electrostatic charge on applicator surface 13. Once charged, applicator surface 13 can be slowly rotated over a bed of fluidized dry particulate (e.g., powdered) medicament 14. Particulate medicament 14 is attracted to and is deposited on applicator surface 13. When a predetermined quantity of particulate medicament 14 is attached to applicator surface 13, dispenser 10 is removed and is ready for use. Means for enhancing and preserving the electrostatic charge may be used. For example, the thin film of metallic aluminum may be coated onto applicator surface 13. Alternatively, a metallic coating may also be applied to the interior of hollow applicator body 11 so that applicator surface 13 operates as an electric capacitor.

As indicated above, medicament 14 is in a dry form. The term "dry", as used herein, is used in its ordinary meaning; i.e., free or relatively free of water or liquid such that there is beneficially no undue moisture or water. Such dry medicaments 14 offers advantages in terms of medicament 14 stability. For example, a dry medicament 14 is not stored and shipped in a solubilized state requiring solvents. Likewise, the transfer of medicament 14 does not require a liquid carrier. Thus, the lack of liquid carriers, diluants and/or solvents typical of dry medicaments 14 results in greater stability of medicament 14. Another advantage of dry medicaments 14 which generally lack carriers, diluants and/or solvents is a reduced response time. Since dry medicament 14 is delivered without these additional ingredients, the concentration of medicament active at the surface of the tissue membrane causes a high concentration gradient across the membrane; thereby causing the medicament active to cross the membrane more quickly.

A further advantage of dry medicaments 14 is the ability to combine various dissimilar medicament actives on a dispenser 10 which would otherwise be incompatible (e.g., in solution, liquid or cream form). For example, disposable dose dispensers 10 of the present invention allow mixing of disparate medicament ingredients which would interact in solution form; thereby convening to a non-beneficial substance during storage and shipping. Each dry medicament active can be sequentially pattern coated onto applicator surface 13 such that they are interspersed. Alternatively, each dry medicament active can be pattern coated onto a particular area (e.g., in dots or stripes) of applicator surface 13.

Figure 2:
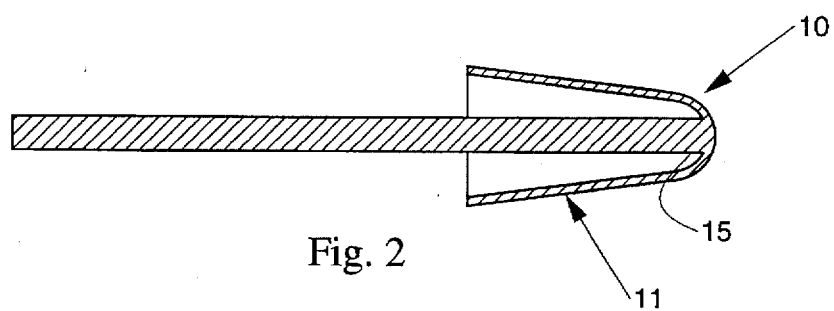
FIG. 2 is a cross-sectional view of the dispenser of FIG. 1.
Figure 3:
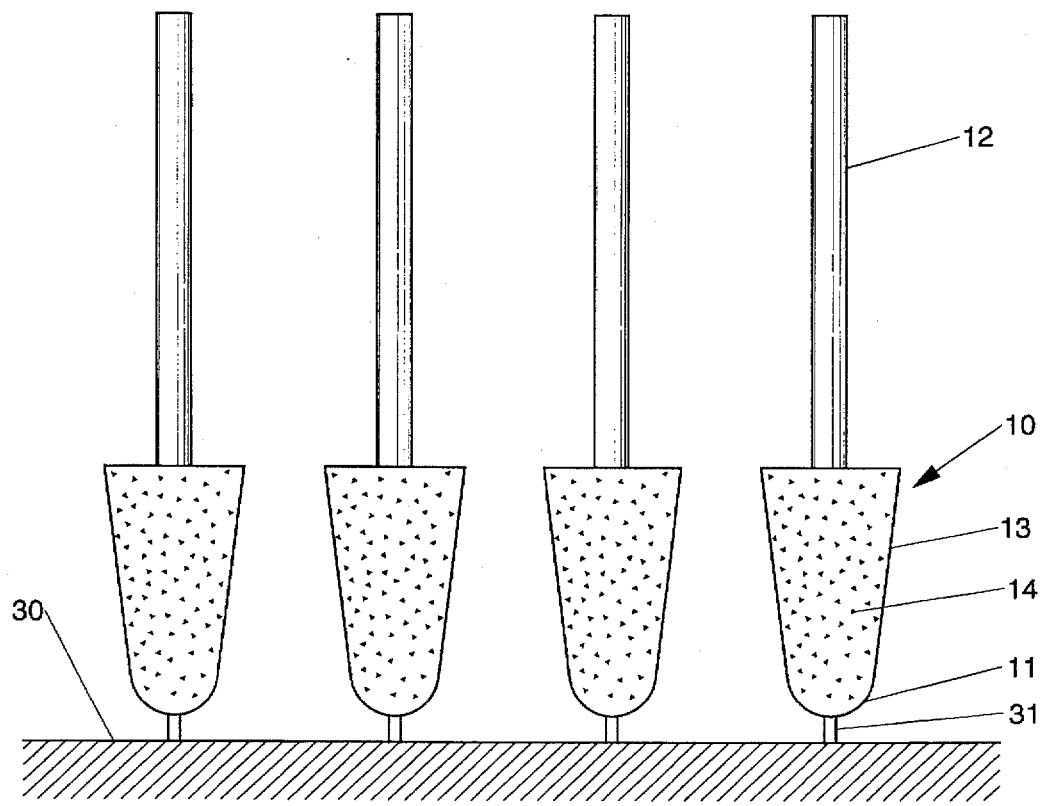
FIG. 3 is a side view of a set of dispensers of FIG. 1 fastened to a carrier means via breakable posts.

FIG. 2 shows a cross-sectional view of disposable unit dose dispenser 10 having a relatively thin shell applicator body 11 integrally molded with handle 10. Applicator body 11 includes applicator surface 13 which may be smooth or ridged; depending upon the application. Disposable dose dispenser 10 may be molded of polymeric materials, including polypropylene, polyethylene and biodegradable polymers (e.g., polycaprolactone or polylactate). As seen in FIG. 3, multiple unit dose dispensers 10 may be attached to a carrier 30 by integrally molding the dispensers 10 with carrier 30 via breakable posts 31. Thus, breakable posts 31 provide a support for disposable unit dose dispensers 10 during shipping and handling. A cover (not seen) for providing protection (e.g., from contact or the atmosphere) for disposable unit dose dispensers 10 during shipping and handling may also be provided. The cover may be a single cover attached to base 30 or individual covers over each applicator surface 13. The particularities of such covers are known in the an and can be, for example, injection molded, plastic shrink wrap or stretch wrap.

To use disposable dose dispenser 10, the user would twist handle 12 of a selected disposable dose dispenser 10 which would shear breakable post 31 releasing the selected disposable dose dispenser 10 from carrier 30. Further manipulating disposable dose dispenser 10 by means of handle 12, the user then inserts the applicator body 13 into a nostril; for example. The friably attached nature of particulate medicament 14 to applicator surface 13 permits particulate medicament 14 to be substantially immediately released from applicator surface 13. In this embodiment, where electrostatic attraction friably attaches particulate medicament 14 to applicator surface 13, this release may be caused by the discharge of the electrostatic charge. Additionally, the friction caused by light mechanical contact with nasal hair and the nasal membrane may serve to release some or all of the particulate medicament 14. Even the aerodynamic action of inspired air may create enough friction to cause the release of some or all particulate medicament 14 from disposable dose dispenser 10. Thus, the release of particulate medicament 14 from applicator surface 13 occurs substantially immediately upon inserting the dispensing device 10 into the nostril. There is no need to wait for the medicament 14 to solubilize to cause release of the medicament 14 from applicator surface 13.

Figure 4:
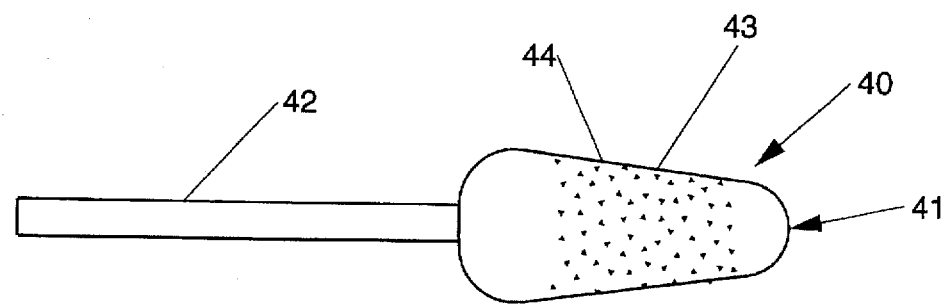
FIG. 4 is a side view of an alternative preferred embodiment of a dispenser for friably releasing a dry particulate medicament of the present invention.
Figure 5:
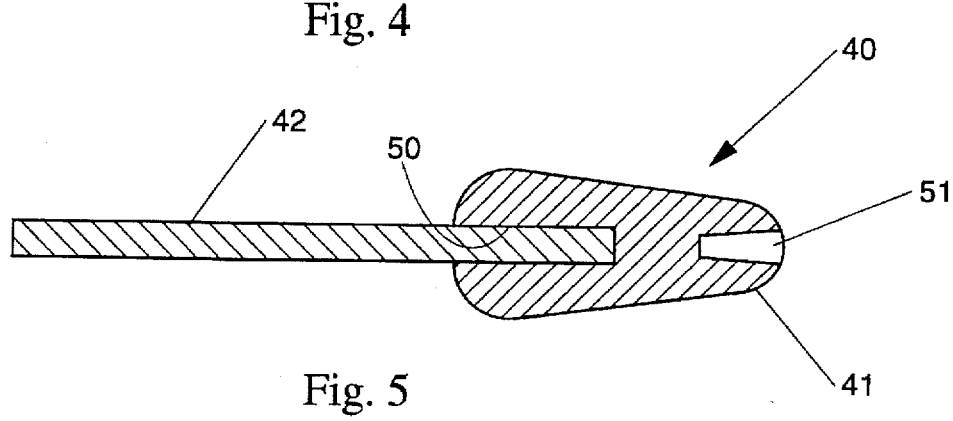
FIG. 5 is a cross-sectional view of the alternative preferred dispenser of FIG. 4.
Figure 6:
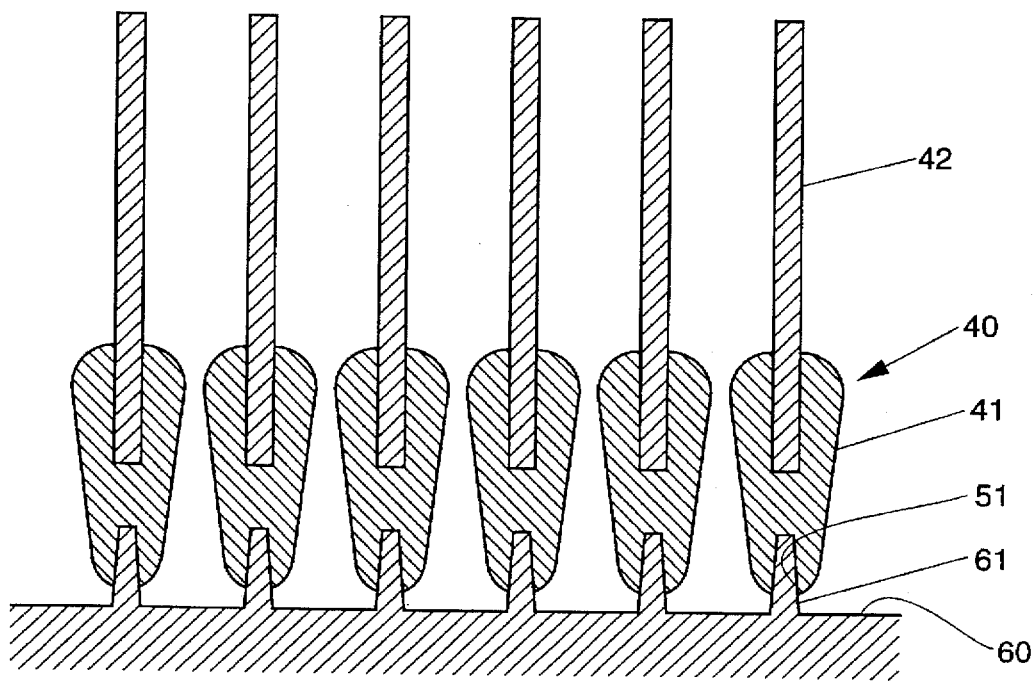
FIG. 6 is a side view of a set of dispensers of FIG. 4 fastened to a carrier means via posts on a carrier mated to corresponding holes in the dispensers.

Referring to FIG. 4, an alternative preferred embodiment of a disposable dose dispenser generally indicated as 40, is illustrated. Disposable dose dispenser 40 comprehends an applicator body 41 and a handle 42. As seen in FIG. 5, applicator body 41 is a generally solid structure which includes a hole 50 for attaching the handle 42. Handle 42 is inserted and secured in hole 50 of applicator body 41 by friction, adhesive or other suitable means. A handle 42 may be provided with each applicator surface 13 as illustrated, or a single reusable handle 42 may be provided for use with each of the applicator surfaces 43. The applicator body 41 may be formed, e.g., of compressed pulp paper. In addition, handle 42 may by constructed of wound paper so as to render the entire dose dispenser 40 flushable and biodegradable. As seen in FIG. 6, a set of disposable dose dispensers 40 is attached to a carrier 60 by means of a press fit of hole 51 in applicator body 41 onto post 61 of carrier 60. A cover (not seen) may provide additional protection for disposable dose dispensers 40 as previously discussed.

Applicator body 41 further comprises an applicator surface 43 and a predetermined unit dose quantity of dry medicament 44 friably attached thereto. Patterns of stripes, dots, or others may be desirable depending upon such desired features as aesthetics, function, or medicament application process. For example, dry medicament 44 may be applied in a pattern of stripes via an ink jet printing process. In one exemplary embodiment of the present invention, an oxymetazoline decongestant and ethyl cellulose binder in an ethyl alcohol carrier may be combined to form a solution having a weight ratio of 2%, 2%, and 96%, respectively. An ink jet printing system may be used to apply this solution to applicator surface 43 formed of medical grade polypropylene (PP). For example, an Image ink jet printer with a standard "G" print head (available from Image, Bourg-les-Alence, France) may be utilized. The alcohol quickly evaporates leaving the oxymetazoline medicament 44 and ethyl cellulose binder in an agglomerated structure of tiny flake-like elements friably attached to each other and the PP applicator surface 43.

To use disposable dose dispenser 40, the user pulls handle 42 of a selected disposable dose dispenser 40 which releases the selected disposable dose dispenser 40 from a mating post 61 of carrier 60. Further manipulating disposable dose dispenser 40 by means of handle 42, the user then inserts the applicator body 41 into a selected nostril, for example. The friably attached nature of the medicament 14 permits the dry medicament 44 to be released from applicator surface 43 in particulate form. In addition to releasing the agglomerated flake-like structures from the applicator surface the friable nature of the medicament 44 allows the ready break-up of the agglomerated structures into small particles. The release and break-up is generally due to the friction caused by light mechanical contact with nasal hair, nasal membrane, and even the aerodynamic action of inspired air. Thus, the release of the medicament 44 from applicator surface 43 occurs substantially immediately upon inserting the dispensing device 40 into the nostril. There is no need to wait for the medicament 44 to solubilize to cause release of the medicament 44 form the applicator surface 43. After use, disposable dose dispenser 40 may be easily disposed of because of the minimal material involved. If a biodegradable material, e,g., pulp paper, is used, disposable dose dispenser 40 may also be toilet flushable.

Figure 7:
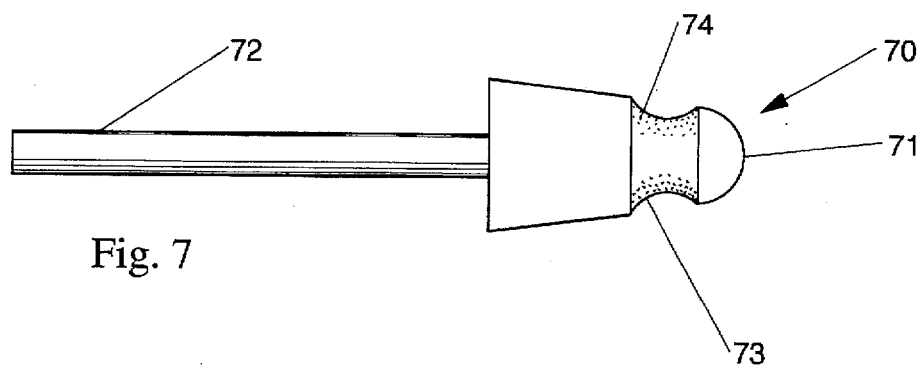
FIG. 7 is a side view of a second alternative preferred embodiment of a dispenser of the present invention.

In another embodiment seen in FIG. 7, there is seen a disposable dose dispenser, generally indicated as 70. Disposable dose dispenser 70 comprises an applicator body 71 and a handle 72 similar in construction to dispenser 10. Applicator body 71 further comprises an applicator surface 73 formed as a circumferential recess in applicator body 71. Applicator surface 73 is shown with a dose quantity of particulate medicament 74. Using such a recessed applicator surface 73 can be advantageous. Locating particulate medicament 74 in a recesses protects particulate medicament 74 from accidental transfer prior to application to the intended body surface. For example, when a cover (not seen) is provided over applicator body 71 the recessed nature of applicator surface 73 prevents the cover from inadvertently prematurely contacting and releasing particulate medicament 74 from applicator surface 73.

In this embodiment, a light adhesive may be pattern coated into the recess housing applicator surface 73. An exemplary light adhesive is the adhesive used in self-sticking removable notes (e.g., Post-it notes). Knowing the characteristics of the adhesive with respect to the particulate medicament 74, the appropriate surface 73 area can be defined for a given medicament 74 to surface 73 application process. For example, the applicator body 71 may be dipped into a fluidized bed of powdered medicament 74 to attract a predetermined dose of particulate medicament 74. Similarly, a predetermined amount of medicament 74 may be directed at applicator surface 73 (e.g., in an air stream) such that a unit dose of particulate medicament 74 becomes adhered to applicator surface 73.

Alternatively, a fairly strong adhesive may be utilized where the particulates themselves of the particulate medicament 74 are frangible. Thus, release of the unit dose of particulate medicament 74 relies upon the breaking of the particulates themselves. Thus, a quantity of medicament 74 which will yield the release of a unit dose of particulate medicament 74 upon breaking during the process of applying medicament 74 to the target tissue can be directed at applicator surface 73 covered by the adhesive (e.g., in a stream of air). Thus, the characteristics of particulate medicament 74 itself may operate to tenuously attach medicament 74 to applicator surface 73.

Figure 8A:
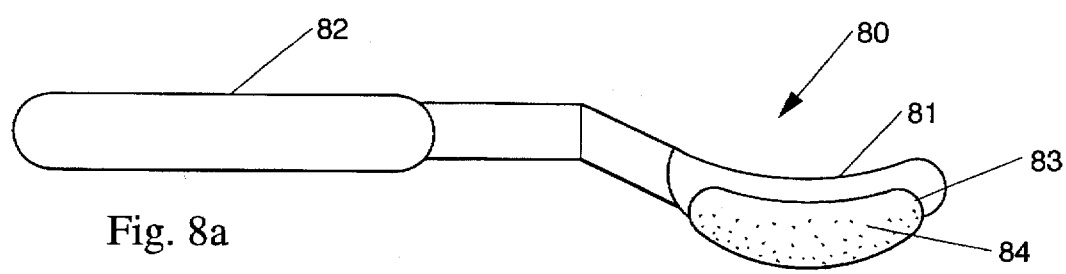
FIG. 8a is a side view of a third alternative preferred embodiment of a dispenser of the present invention.
Figure 8B:
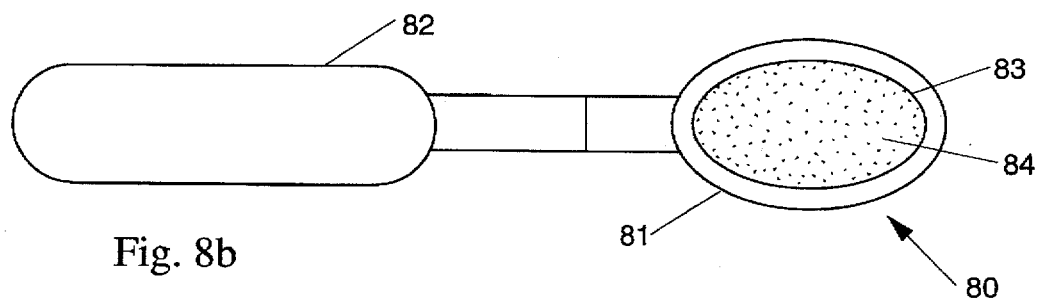

In another embodiment seen in FIG. 8A and 8B, there is seen a disposable dose dispenser, generally indicated as 80. Disposable dose dispenser 80 comprises an applicator body 81 and a handle 82, having a generally spoon-like shape. Applicator body 81 further comprises a raised applicator surface 83 formed therein with a dose quantity of particulate medicament 84 tenuously attached thereto. Dry medicament 84 may he friably attached to applicator surface 83 via any of those previously discussed. This raised applicator surface 83 may he provided by simply shaping the body 81 of the dispenser 80 with the raised surface 83; or printing medicament 84 on another surface (not seen) and adhering that surface to the applicator body 81 (e.g., as discussed below with respect to FIG. 9).

Figure 9:
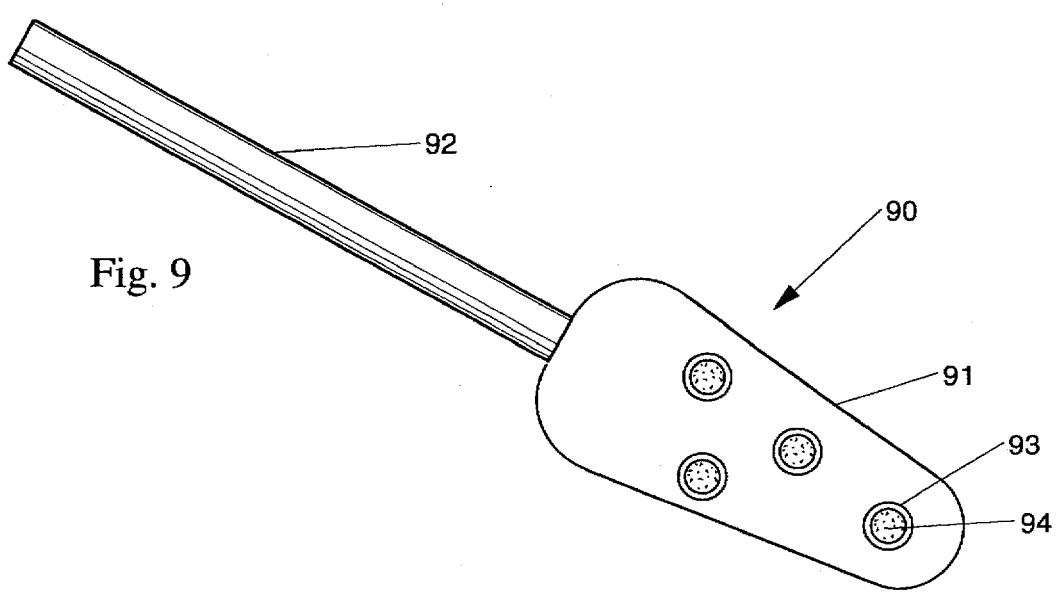
FIG. 9 is a side view of a fourth alternative preferred embodiment of a dispenser of the present invention.

Referring to FIG. 9, there is seen an alternative disposable dose dispenser generally indicated as 90. Disposable dose dispenser 90 comprises an applicator body 91 and a handle 92 similar in construction to dispenser 40. Applicator body 91 further comprises a set of raised applicator surfaces 93 located about applicator body 91. In aggregate, the raised surfaces form applicator surface 93 and contain a unit dose quantity of particulate medicament 94 friably attached thereto. Dry medicament 94 may be friably attached to applicator surface 93, for example, as previously described. Raised applicator surface 93 may be, e.g., adhesively secured circular elements of polymeric material; such as polyethylene film. Alternatively, the pressed paper of the applicator body 91 could simply he compressed into a mold including the raised applicator surface 93. Thus, applicator surface 93 and applicator body 91 may he of different or identical material.

Referring to FIG. 10, there is seen a disposable dose dispenser, generally indicated as 100. Disposable dose dispenser 100 comprises an applicator body 101 and a handle 102. Applicator body 101 further comprises an applicator surface 103 and a unit dose quantity of dry medicament 104. In FIG. 11 there is shown a cross-sectional view of disposable dose dispenser 100 nested within a similar disposable dose dispenser 110. Disposable dose dispenser 100 is molded with a cavity 105. At the opening of cavity 105 is internal ring 107. Disposable dose dispenser 110 is molded in the same form as disposable dose dispenser 100 and has cavity 115 and internal ring 117 similar to cavity 105 and internal ring 107, respectively.

In the stacked condition, applicator body 103 of disposable dose dispenser 100 is located within cavity 115 of disposable dose dispenser 110 wherein internal ring 117 sealingly engages external ring 106. Friction, or alternatively, a detent system between internal ring 117 and external ring 106 may be employed to secure disposable dose dispenser 110 to disposable dose dispenser 100. In the stacked condition, internal cavity 115 of the upper disposable dose dispenser 110 provides protection to the applicator surface 103 and dry medicament 104 of the lower disposable dose dispenser 100. Mounted on upper disposable dose dispenser 110 is cap 120 wherein internal ring 127 sealingly engages external ring 116. Cap 120 provides protection to the applicator surface 113 and dry medicament 114 of the uppermost disposable dose dispenser 110. If additional disposable dose dispensers are added to the stack, each upper disposable dose dispenser provides protection to the applicator surface and particulate medicament of each lower disposable dose dispenser thereby providing a simple means to deliver and protect the disposable dose dispensers during shipping, handling, and storage. Just prior to actual use, the user retracts the lowermost disposable dose dispenser 100, disengaging the seal between seal ring 107 and internal ring 117 using handle 102 as a gripping surface. Thus, the dispenser 100 is ready for substantially immediate release of a unit dose quantity of dry medicament 104 in a particulate form from applicator surface 103, as discussed previously.

Referring to FIGS. 12 and 13, another preferred embodiment of a dose dispenser of the present invention is illustrated. Dose dispenser 200 can be utilized to apply, e.g., a topical vaginal medicament. Dose dispenser 200 comprises applicator wand 210 and shell 220. Applicator wand further comprises applicator surfaces 213, a predetermined unit dose quantity of medicament 214, bulb 215, guide rails 216, and catch ring 217. Shell 220 further comprises sheath 221, handle 222, and limit ring 223. Particulate medicament 214 is tenuously attached to the applicator surfaces 213, e.g., as previously described. In use, dose dispenser 200 is inserted into the vagina. Although bulb 215 facilitates insertion, a light coating of suitable internal lubricant on bulb 215 and sheath 221 may be desirable. Once inserted fully, handle 222 is manually retracted. Since bulb 215 is larger than sheath 221, bulb 215 tends to be retained by the vaginal walls. As a result, shell 220 slides relative to applicator wand 210 exposing medicament 214 to the vaginal wall wherein medicament 214 is substantially immediately transfers from applicator surfaces 213 to the vaginal wall. Applicator surfaces 213 are slightly recessed relative to guide rails 216 thereby preventing contact and wiping of medicament 214 from applicator surfaces 213 by limit ring 223 of shell 220. Of course, the location of the recess and protruding elements can alternatively be reversed so that the cover is held away from a non-recessed applicator surface by tabs on the cover which ride in groves on applicator body. Retraction of shell 220 relative to applicator wand 210 continues until catch ring 217 engages limit ring 223. Release and transfer of particulate medicament results from friction developed between the mucous membrane of the vaginal cavity and particulate medicament 14 located on applicator surface 13 as previously described. At this point, further retraction of handle 222 causes dose dispenser 200 to be retracted from the vagina.

Although particular embodiments of the present invention have been illustrated and described, modifications may be made without departing from the teachings of the present invention. For example, applicator body may include a tape advance mechanism for advancing disposable applicator surfaces holding a predetermined dose of particulate medicament. As another example, an indexed cover may be utilized to expose only a portion of the applicator surface housing a predetermined quantity of particulate medicament for one nostril, then indexing to expose the predetermined quantity for the other nostril. Accordingly, the present invention comprises all embodiments within the scope of the appended claims.

What is claimed is:

1. An applicator for dispensing a dry medicament in particulate form comprising:

a) a liquid resistant applicator surface;

b) a handle connected to said applicator for manually manipulating said applicator surface; and c) a friable dry medicament attached to said applicator surface by a bond, said friable dry medicament and said bond being sufficiently weak to release particles of said friable dry medicament smaller than 1 mm in size upon frictional contact of said friable dry medicament by a body surface, such that some of said particles transfer from said applicator surface substantially immediately to said body surface without first dissolving in a body fluid, and wherein said friable dry medicament is located within a plurality of recesses within the applicator.

2. The applicator of claim 1 wherein a friable dry medicament is located within at least one of said plurality of recesses which is different than said friable dry medicament located in other of said plurality of recesses.

3. An applicator for dispensing a dry medicament in particulate form comprising:

a) a liquid resistant applicator surface;

b) a handle connected to said applicator for manually manipulating said applicator surface; and c) a friable dry, medicament attached to said applicator surface by a bond; said friable dry, medicament and said bond being sufficiently weak to release particles of said friable dry medicament smaller than 1 mm in size upon frictional contact of said friable dry medicament by a body surface, such that some of said particles transfer from said applicator surface substantially immediately to said body surface without first dissolving in a body fluid, and wherein said friable dry medicament is located on a plurality of raised areas located on the applicator.

4. The applicator of claim 3 wherein a friable dry medicament is located on at least one of said plurality of raised areas which is different than said friable dry medicament located on other of said plurality of raised areas.

5. An applicator for dispensing a dry, medicament in particulate form comprising:

a) a liquid resistant applicator surface;

b) a handle connected to said applicator for manually manipulating said applicator surface; and c) a friable dry, medicament attached to said applicator surface by a bond, said friable dry medicament and said bond being sufficiently weak to release particles of said friable dry medicament smaller than 1 mm in size upon frictional contact of said friable dry medicament by a body surface, such that some of said particles transfer from said applicator surface substantially immediately to said body surface without first dissolving in a body fluid, and further comprising a slidable cover attached to said applicator which protects said friable dry medicament located on said applicator surface during insertion of said applicator into a body cavity, and retracts to expose said friable dry medicament on said applicator surface during removal of said applicator.

6. An applicator for dispensing a dry medicament in particulate form to a nostril, said applicator comprising:

a) a liquid resistant applicator surface having a frusto-conical shape;

b) a handle connected to said applicator for manually manipulating said applicator surface; and c) a friable dry medicament attached to said applicator surface by a bond, said friable dry medicament and said bond being sufficiently weak that particles of said friable dry medicament less than 1 mm in size are released from said applicator surface upon inhalation when said applicator is placed within a nostril, some of said particles being transferred substantially immediately from said applicator surface to said nostril without first dissolving in nostril mucous.

7. A method of delivering a friable dry medicament in particulate form to a nostril, said method comprising the steps of inserting into said nostril an applicator having an applicator surface coated with said friable dry medicament and inhaling such that said friable dry medicament breaks into particles, said particles being released from said applicator surface by a combination of frictional contact with surfaces of said nostril and aerodynamic action of inspired air, said release occurring substantially immediately without first dissolving said friable dry medicament in nostril mucous.

* * * * *